US006175054B1

(12) United States Patent
Jacques

(10) Patent No.: US 6,175,054 B1
(45) Date of Patent: Jan. 16, 2001

(54) WATER SOLUBLE FILMS

(75) Inventor: Elizabeth Jacques, Chester (GB)

(73) Assignee: Bristol-Myers Squibb Company, New York, NY (US)

( * ) Notice: Under 35 U.S.C. 154(b), the term of this patent shall be extended for 0 days.

(21) Appl. No.: 09/066,400

(22) PCT Filed: Oct. 31, 1996

(86) PCT No.: PCT/EP96/04780

§ 371 Date: Jul. 13, 1998

§ 102(e) Date: Jul. 13, 1998

(87) PCT Pub. No.: WO97/16212

PCT Pub. Date: May 9, 1997

(30) Foreign Application Priority Data

Nov. 1, 1995 (EP) .................................................... 9522314

(51) Int. Cl.⁷ ...................................................... A61F 13/00
(52) U.S. Cl. .................. 602/48; 602/41; 602/42
(58) Field of Search ...................... 602/41–59; 424/443, 424/445, 446, 447, 448; 128/888, 889

(56) References Cited

U.S. PATENT DOCUMENTS 5,681,579 * 10/1997 Freeman .
5,735,812 * 4/1998 Handy .

* cited by examiner

*Primary Examiner*—Kim M. Lee
(74) *Attorney, Agent, or Firm*—Theodore R. Furman, Jr.; John M. Kilcoyne

(57) ABSTRACT

A water soluble film having a thickness of from 0.03 mm to 0.5 mm comprising a water soluble polymer and an active substance.

8 Claims, No Drawings

WATER SOLUBLE FILMS

The invention relates to water soluble films and in particular water soluble films used to deliver an active substance co a wound.

It is known to use active substances such as antioxidants, deodorants, perfumes or pharmacologically active substances in hydrocolloid wound dressings. In particular it is known to include actives as optional ingredients in a composition forming the wound and skin contacting layer of a wound dressing Such compositions is described in EP-B-0092999, EP-B-130061 or EP-B-190814. Typically the composition comprises a homogeneous blend of hydrocolloid to absord exudate from the wound and an adhesive such as polyisobutylene to stick the dressing to the surrounding skin. Generally the delivery of the active substance from such a dressing is unpredictable and slow because the active is distributed throughout the adhesive layer and not concentrated at the wound and skin contacting surface.

An alternative wound dressing to a hydrocolloid based dressing is one based on fibres sometimes referred to as super-absorbant fibres. Such fibres are described in WO-A-93/12275 which describes modified cellulose fibres and in PCT/GB/9400102 which describes reprocessed alginate fibres. In general, it is difficult to incorporate active substances into such fibres because of the processes used in their manufacture. For example in WO 93/12275 cellulose based fibres are produced according to a method which includes a step in which the fibres are washed with a solution containing a high proportion of industrial alcohol. The use of such a wash on fibres comprising an active substance may cause inactivity or a reduction in activity of the substance.

We have now found that it is possible to incorporate active substances into water soluble films that can be used as part of or in addition to a wound dressing to deliver active substances to a wound.

Accordingly the invention provides a water soluble film having a thickness of from 0.03 mm to 0.5 mm comprising a water soluble polymer and an active substance. Preferably the film thickness is from 0.01 mm to 0.1 mm.

Because of its thinness such a film may predictably and rapidly release active substance into a wound. Such a film may be incorporated into a wound dressing as a separate layer which contacts the wound.

Accordingly the invention provides a wound dressing comprising a water soluble film said film comprising a water soluble polymer and an active substance.

Such a film may be integrally formed as an outer layer of a dressing so as to allow rapid delivery of an active substance to the wound from the dressing. This has the advantage that the active is not subjected co the processing regime of the fibre.

Water soluble polymers suitable for use in the present invention include sodium carboxymethylcellulose and particularly those sodium carboxymethylcelluloses having a viscosity in the range of 200 to 800 mPas, sodium alginate, hyaluronic acid and in particular the sodium salt, hydroxypropylcellulose, polyvinylalcohol, and hydroxyethylcellulose. Preferably the water soluble polymer is present at a level of from 20% to 99.5%, more preferably 30% to 94.5% and most preferably 60% to 90% by weight of the dry film.

Active substances suitable for use in the present invention include antibiotics such as polymyxin B and zinc bacitracin, antimicrobials such as metronidizole and silver sulphur diazine, broad spectrum antimicrobials such as PVPI and free radical scavengers such as vitamin A and vitamin E. Preferably the active substance is present at a level of from 0.5% to 10%, more preferably 0.5% to 40% and most preferably 0.5% to 5% by weight of the dry film.

Films according to the present invention preferably comprise a plasticiser to increase the flexibility of the film. Examples of plasticisers suitable for use in films of the present invention include propylene glycol. glycerol, depanthanol, sodium lactate, polyethylene glycol and sorbitol. When present the plasticiser is preferably present at a level of from 5% to 80%, more preferably 30% to 60% by weight of the dry film.

Films according to the present invention preferably comprise a deodorising agent for example chlorophyllin or Grillocin™. When present the deodorising agent is preferably present at a level of from 0.5% to 15%, more preferably 1% to 10% by weight of the dry film.

Wound dressings according to the present invention comprising a water soluble film comprising a water soluble polymer and an active substance preferably comprise a substrate made from fibres of cellulose, alginate or hyaluronic acid to which the film is attached or a substrate of hydrocolloid such as that described in EP 92999B co which the film is attached.

The following examples illustrate preferred embodiments of the invention.

EXAMPLE 1

An aqueous solution of the following components was made by dissolving the components in water:

|  | % by weight |
| --- | --- |
| Sodium CMC | 6% |
| Propylene Glycol | 4% |
| Silver sulphadiazine | 0.1% |
| Water to | 100% |

The solution was allowed co de-aerate either by using a vacuum or with time. The solution was then coated onto a suitable release paper (for example Melinex™) at a coating thickness of approximately 1 mm. Fibrous substrates such as KALTOSTAT™ an alginate fibre dressing ex CV Laboratories Ltd and a fibrous dressing made as described in WO 9416746 was then placed on the film solution and caused to dry by placing them in an oven at 40 to 80° C. for approximately half an hour to a final film thickness of about 0.1 mm.

The resulting dressing was irradiated by an a source of 2SKGy and packaged in a polythene backed foil pouch. The irradiation had no detrimental effects on the dressing.

The dressings dissolved readily in water or in saline solution, were opaque and very flexible which allowed them to be cut using scissors. The dressings were also sufficiently robust that they could be torn by hand. For the fibrous dressings without the water soluble film applied this was not possible.

EXAMPLE 2

The method of Example 1 was repeated with the following aqueous solutions to make wound dressings according to the invention.

| Solution 1 | % by weight |
|---|---|
| Sodium CMC | 6 |
| Glycerol | 14 |
| Sodium silver diazine | 0.2 |
| water to | 100% |

The resulting film had a tacky surface making it readily adhere co the fibrous substrates or dry skin.

| | % by weight |
|---|---|
| Solution 2 | |
| Sodium CMC | 6 |
| Propylene glycol | 4 |
| Metronidazole | 0.08 |
| Water to | 100% |
| Solution 3 | |
| Sodium CMC | 6 |
| Propylene Glycol | 4 |
| Zinc bacitracin | 0.0079 |
| Polymyxin B | 0.0435 |
| Water to | 100% |
| Solution 4 | |
| Hydroxypropylcellulose | 20 |
| Zinc bacitracin | 0.026 |
| Polymyxin B | 0.145 |
| Water to | 100% |
| Solution 5 | |
| Hydroxypropylcellulose | 5 |
| Glycerol | 1.5 |
| Povidone Iodine | 3.25 |
| Water to | 100% |

EXAMPLE 3

Using the method of Example 1 the solution of Example 1, solution 2 and solution 5 were coated onto separate release papers and dried. Fibrous dressings were not placed on the films but instead, the resulting films were then placed on the wound contacting surface of a hydrocolloid substrate such as GRANUFLEX ex ConvaTec as described in EP92999B so that only the central portion of the surface of the substrate was covered by the film. This allows the film to contact the wound without affecting the adhesive properties of the substrate on the surrounding skin.

What is claimed is:

1. A multilayered wound dressing comprising:
   (a) a wound contact layer which is a water soluble film, having a thickness of from about 0.01 mm to about 0.5 mm, comprising the sodium salt of hyaluronic acid and an active substance to be released into a wound; and
   (b) a fibrous layer overlying said wound contact layer.

2. A multilayered wound dressing as claimed in claim 1 wherein the fibrous layer is a layer of non-woven-fabric.

3. A multilayered wound dressing as claimed in claim 1 wherein the hyaluronic acid is present at a level of from about 20% to about 99.5% by weight of the wound contacting layer.

4. A multilayered wound dressing as claimed in claim 1 wherein the fibrous layer comprises fibers selected from the group consisting of cellulose, alginate and hyaluronic acid fibers.

5. A multilayered wound dressing comprising:
   (a) a wound contact layer which is a water soluble film, having a thickness of from about 0.03 mm to about 0.1 mm, comprising the sodium salt of hyaluronic acid and an active substance to be released into a wound; and
   (b) a fibrous layer overlying said wound contact layer.

6. A multilayered wound dressing as claimed in claim 6 wherein the fibrous layer is a layer of non-woven-fabric.

7. A multilayered wound dressing as claimed in claim 5 wherein the hyaluronic acid is present at a level of from about 20% to about 99.5% by weight of the wound contacting layer.

8. A multilayered wound dressing as claimed in claim 5 wherein the fibrous layer comprises fibers selected from the group consisting of cellulose, alginate and hyaluronic acid fibers.

* * * * *